(12) United States Patent
Antonelli et al.

(10) Patent No.: US 6,259,108 B1
(45) Date of Patent: Jul. 10, 2001

(54) FINGERPRINT IMAGE OPTICAL INPUT APPARATUS

(75) Inventors: Keith Antonelli; Geoffrey Vanderkooy; Timothy Vlaar; Guy Immega, all of Vancouver (CA)

(73) Assignee: Kinetic Sciences Inc. (CA)

( * ) Notice: Subject to any disclaimer, the term of this patent is extended or adjusted under 35 U.S.C. 154(b) by 0 days.

(21) Appl. No.: 09/169,008

(22) Filed: Oct. 9, 1998

(51) Int. Cl.[7] .................................................. G06K 9/00
(52) U.S. Cl. ............................. 250/556; 356/71; 382/126
(58) Field of Search ........................... 250/556; 356/71; 382/126, 127

(56) References Cited

U.S. PATENT DOCUMENTS

| | | | |
|---|---|---|---|
| 4,784,484 | * 11/1988 | Jensen | 356/71 |
| 4,832,485 | 5/1989 | Bowles. | |
| 5,448,649 | 9/1995 | Chen et al. | |
| 5,619,586 | * 4/1997 | Sibbald | 382/127 |
| 5,942,761 | * 8/1999 | Tuli | 250/556 |
| 6,011,860 | * 1/2000 | Fujieda et al. | 382/126 |

FOREIGN PATENT DOCUMENTS

| | | |
|---|---|---|
| 0098607 | 7/1983 | (EP). |
| 96/13742 | 10/1995 | (WO). |

* cited by examiner

Primary Examiner—Stephone B. Allen
(74) Attorney, Agent, or Firm—Mark M. Yang; Randolph A. Smith

(57) ABSTRACT

A fingerprint optical input apparatus comprises a contact image sensor for viewing a moving finger and providing a high contrast image. A narrow strip of the fingerprint touching a transparent platen is illuminated by sheet of collimated light at an oblique angle to the surface. The fingerprint image is viewed by frustrated total internal reflection by a GRIN rod lens array and projected onto a linear array sensor. Various embodiments of the platen provide a compact design by using TIR or mirror reflections of the fingerprint image.

25 Claims, 10 Drawing Sheets

FINGERPRINT IMAGE OPTICAL INPUT APPARATUS

TECHNICAL FIELD

This invention relates to a method of creating electronic images of a finger or other object with ridges and the like, and a compact optical apparatus to project high contrast image slices of a fingerprint onto sensors.

BACKGROUND

The prior art for contact image sensors is exemplified by U.S. Pat. No. 5,214,273 ("the '273 patent") which issued May 25, 1993 for an invention called "Contact Image Sensor." A second example of prior art is U.S. Pat. No. 5,331,146 ("the '146 patent") which issued Jul. 19, 1994 for an invention called "Contact-type Image Sensor for Generating Electric Signals Corresponding to an Image Formed on a Document." Unlike the present invention, the '273 patent and the '146 patent do not employ frustrated total internal reflection (FTIR) to view a high contrast fingerprint.

The prior art for fingerprint sensors is exemplified by U.S. Pat. No. 4,784,484 ("the '484 patent") which issued Dec. 4, 1986 for an invention called "Method and Apparatus for Automatic Scanning of Fingerprints." Unlike the present invention, the '484 patent uses a separate sensing means to measure the speed of finger motion. Also, unlike the present invention, the '484 patent does not teach the use of FTIR to view a high contrast image of the fingerprint. Finally, unlike the present invention, the '484 patent does not employ a gradient index rod lens array or an array of relay lens pairs.

The prior art for fingerprint sensors is also exemplified by U.S. Pat. No. 5,619,586 ("the '586 patent") which issued May 3, 1995 for an invention called "Method and Apparatus for Producing a Directly Viewable Image of a Fingerprint." The '586 patent shows prior art employing FTIR to obtain a high contrast fingerprint image. However, unlike the present invention, the '586 patent shows imaging of the entire fingerprint at once as an area image, instead of a narrow strip image projected onto a linear array sensor. Also, unlike the present invention, the '586 patent does not show the use of gradient index rod lenses or relay lenses to image the fingerprint.

The prior art for fingerprint sensors is also exemplified by U.S. Pat. No. 5,096,290 ("the '290 patent") which issued Mar. 17, 1990 for an "Apparatus for Imaging Fingerprint Using Transparent Optical Means Having Elastic Material Layer." Unlike the present invention, the '200 patent covers an elastic layer for the entire area of the fingerprint, rather than a narrow strip of the fingerprint.

SUMMARY OF INVENTION

The invention provides a fingerprint image optical input apparatus in the form of a contact image sensor (CIS) which projects high contrast image slices onto a linear array sensor. Novel optics is employed to provide a high contrast image by means of FTIR of the fingerprint which is projected by a GRIN (GRadient INdex of refraction) lens array onto a linear array sensor.

The generally preferred embodiment is a miniaturized CIS sensor arranged to view the width of the moving fingerprint as it is wiped over the optically transparent platen of the sensor. To view the fingerprint, light must be introduced inside the platen. Light from the light source may be introduced inside the transparent platen through a flat or curved surface, which acts as a lens to help collimate the light so that it forms a flat sheet of light the width of the linear array sensor. Once introduced, the light may be directed inside the platen by using total internal reflection (TIR) or reflections from a mirror-like surface or surfaces. The use of reflections to direct the light inside the platen allows the light source to be located anywhere convenient, such as on a printed circuit board; the location of the light source can alter the form of the platen, or allow the platen to be made more compactly. The reflective surfaces or TIR surfaces of the platen can be slightly rough, not perfectly flat, to partially diffuse the light beam and thus cause more even lighting of the fingerprint.

A high contrast image may be obtained by viewing the fingerprint through the transparent platen at an oblique angle; the fingerprint image is then focused by a GRIN lens array onto a linear sensor array. Alternatively, the GRIN lens or other focusing means can be arranged to view reflected images of the fingerprint, and to project reflected images onto the linear array sensor. To provide a high contrast image of the fingerprint, light is directed at an angle to the top interior surface of the platen (typically 45 degrees or more to a line normal to the surface of the platen, depending on the index of refraction of the platen, which is advantageously greater than 1.5), where it is reflected by TIR if no fingerprint is present. Where the fingerprint ridges touch the top surface of the platen, light is not reflected, due to FTIR at the surface of the platen causing absorption of light, resulting in a dark pattern for the fingerprint ridges and bright light at the fingerprint valleys, which are reflected by TIR from the interior of the platen. Foreshortening effects can be accommodated by image processing.

The total internal reflection surface of the platen can be raised strip to increase the pressure of the finger on the imaging surface, thereby giving better contact for total internal reflection. The platen surface or raised portion can also be constructed of silicone or some other material with optical wetting or low friction properties to improve imaging or finger movement respectively. A liquid reservoir can be integrated into the platen or an adjacent surface to allowing wetting of the finger with oil or other liquid to improve the total FTIR imaging, as well as lubricating the finger for smooth motion. The platen itself can be part of the protective housing of the sensing elements. Surfaces of the platen can be coated in a light absorbing material to absorb stray light, thus reducing the noise at the sensor element The high contrast fingerprint image is viewed by a GRIN lens array, or alternatively a relay lens pair array, or any other functionally equivalent means that creates a series of coherent overlapping images. The GRIN lens array looks at an oblique angle opposite to the incoming light; the narrow fingerprint strip image is focused by the GRIN lens array onto the width of a linear array sensor, which may have one linear array of light sensing pixels or two or more parallel linear arrays of light sensing pixels. The advantages of this arrangement are that a very compact optical system can be achieved which provides fingerprint images which have low distortion, high resolution and large format size.

The CIS sensor for fingerprint imaging can be arranged in several novel configurations, which can be optimized for different applications and manufacturing techniques. For those skilled in the art of design of optical components, the different features of various configurations may be utilized or combined, and other materials, components or technologies may used or combined to achieve substantially similar fingerprint imaging systems.

BRIEF DESCRIPTION OF FIGURES

Further objects, features and advantages of the present invention will become more readily apparent to those skilled in the art from the following description of the invention when taken in conjunction with the accompanying drawings, in which.

DESCRIPTION

Figure 1A:
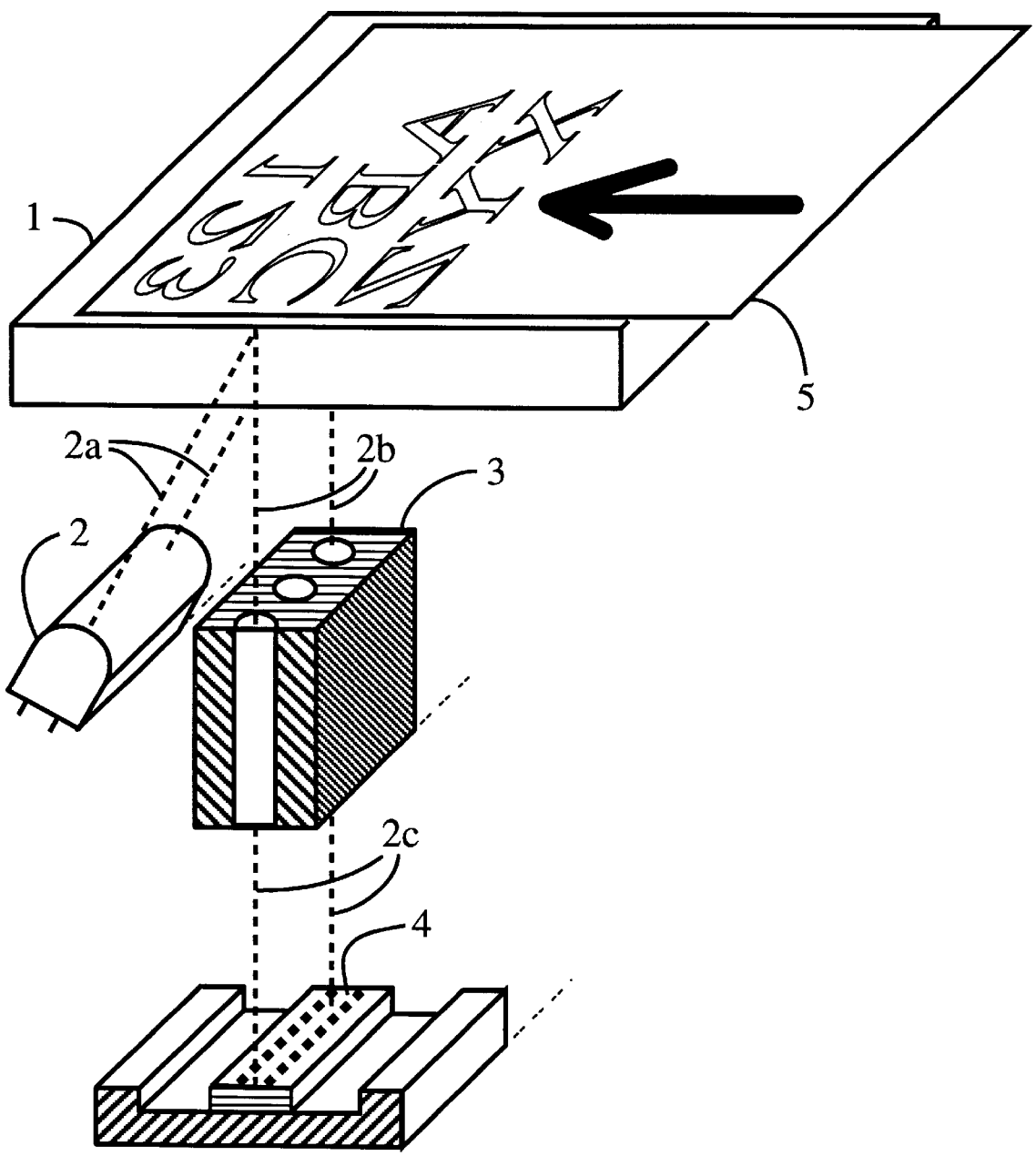
FIG. 1A shows a cut-away, isometric depiction of a side view of the prior art contact image sensor, similar to those commonly used in facsimile machines, viewing a horizontally moving sheet of paper through a GRIN rod lens array and projecting a narrow strip image onto a linear array sensor.

In FIG. 1A a basic CIS (Contact Image Sensor) is shown, which is commonly used in prior art facsimile machines and sheet-feed document scanners. A CIS imager is comprised of four basic components, which include a transparent platen, light source, lens array, and linear array sensor.

Figure 1B:
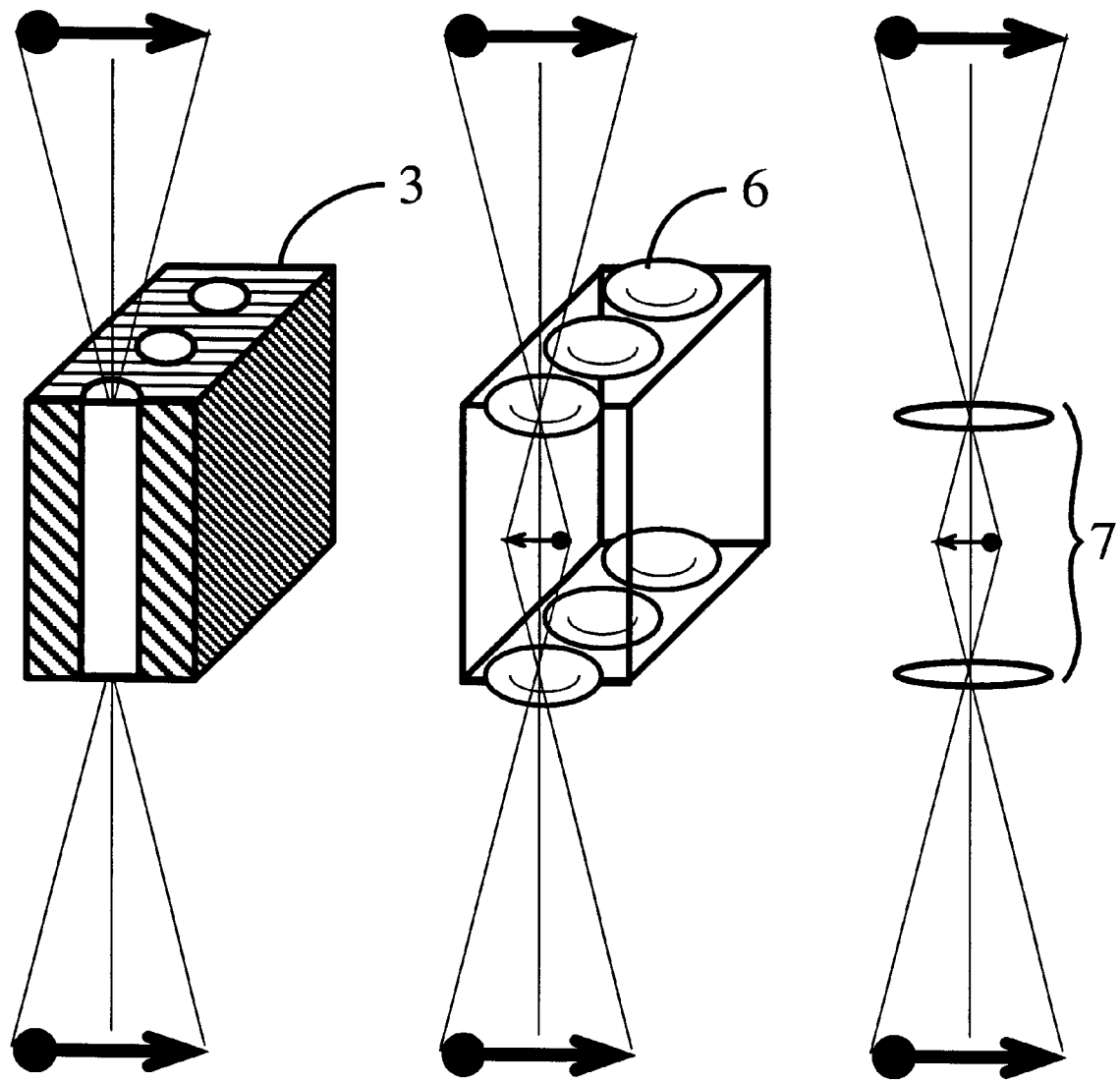
FIG. 1B shows a comparison of a prior art GRIN rod lens array with a functionally equivalent array of relay lens pairs, with an optical ray diagram which depicts the well known image transfer function of relay lenses.

In FIG. 1A the platen 1 is made of transparent glass or plastic, or other suitable transparent material. The light source 2, is conveniently an array of light emitting diodes (LEDs) or any other suitable source of light such as an electro-luminescent strip or miniature fluorescent tube. The lens system is typically a GRIN lens array 3, or it could be replaced by a relay lens array 6 as shown in FIG. 1B. The linear array optical sensor 4, with a single linear array, or two or more parallel rows of light sensing pixels, may use CCD (charge coupled device) pixels, or may use CMOS (complementary metal oxide semiconductor) APS (active pixel sensing) pixels, photo-diode pixels, or any other linear array of light sensing or infrared sensing pixel technology. The width of platen 1, light source 2, GRIN lens array 3 and linear array sensor 4 may be any convenient length, suited to the imaging task at hand.

In FIG. 1A, the CIS sensor is shown imaging a printed sheet of paper 5 which is moved across the platen 1. For facsimile machines and document scanners, paper 5 is mechanically moved across the platen; alternatively, the CIS sensor may be mechanically moved beneath paper 5 on a fixed platen. In the generic configuration of the CIS sensor, light source 2 shines light beam 2a through transparent platen 1 and illuminates the object, such as printed letters on paper 5. Some light 2b is then scattered and reflected from paper 5 and is viewed by GRIN lens array 3 and focused as light 2c onto linear array sensor 4. An electronic gray scale image is gathered line by line by the linear array sensor 4, and is subsequently stored, altered, processed, interpreted, transmitted, displayed, printed or otherwise used.

When a finger is dragged across platen 1 of FIG. 1A (instead of a paper document), an additional sensing means must be used to measure the speed of the finger across the platen and the fingerprint image which is obtained by the CIS sensor will have very low contrast between the fingerprint ridges and valleys. The low contrast causes difficulties in interpreting the significant features of the fingerprint image, making such an image not optimum for fingerprint matching or verification. However, image enhancement techniques may by used to produce a fingerprint imaging system using a standard CIS sensor.

FIG. 1B compares GRIN lens array 3 with relay lens array 6, which is comprised of a linear array of relay lens pairs. In this diagram, relay lens array 6 is the functional equivalent of GRIN lens array 3, which is a 1:1 imager (no magnification, de-magnification or image inversion). The GRIN lens array 3 and relay lens array 6 both create a series of overlapping coherent images to create a single narrow image the width of the array. The general optical properties of a relay lens is shown schematically with relay lens pair 7, whereby an image is transmitted, or relayed, to the focal plane without change in size or orientation. In contrast, GRIN lens array 3 utilizes optical fibers as rod lenses to refract the image, to achieve the same optical result. For all CIS imaging systems, including those designed for imaging the fingerprint, a suitably designed relay lens array may be substituted for a GRIN lens array.

Figure 2:
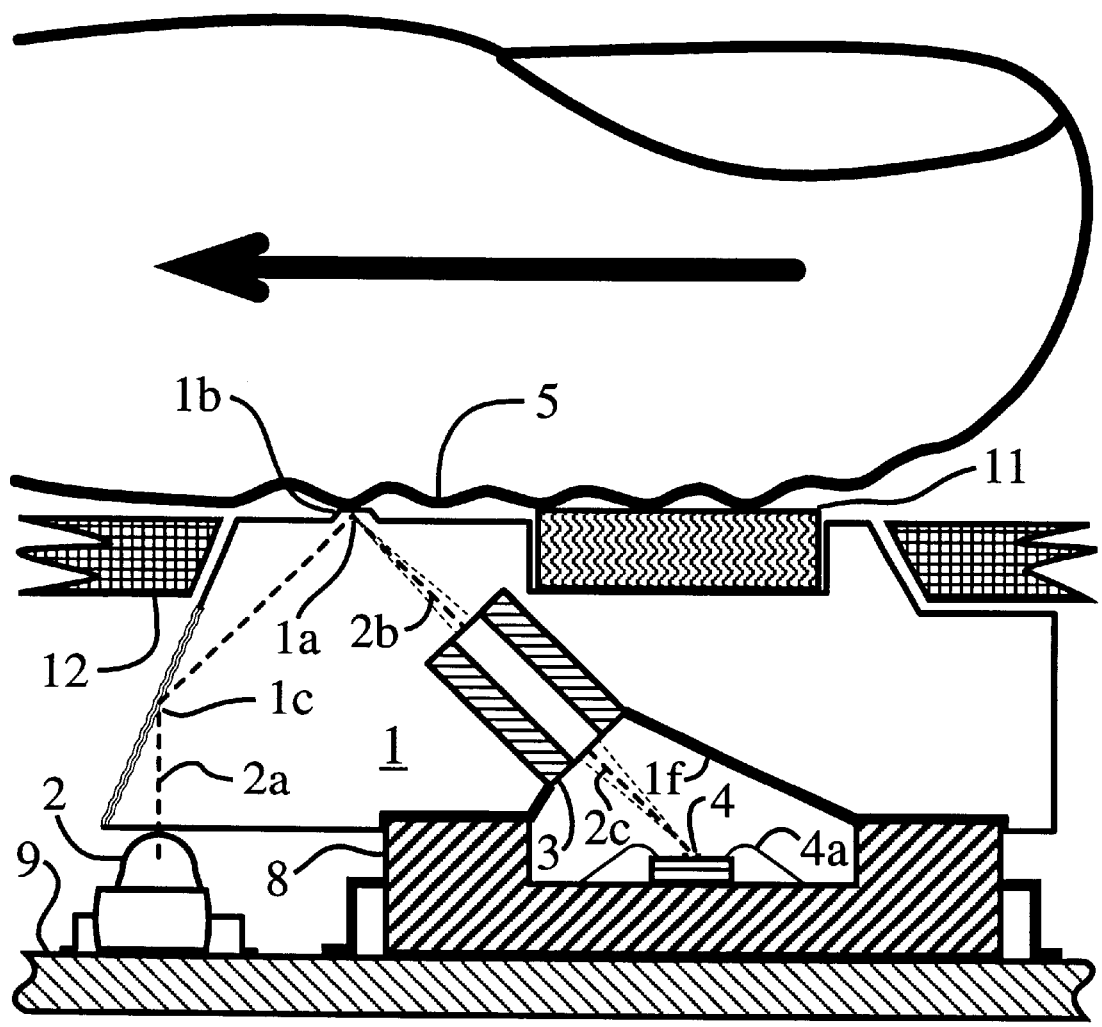
FIG. 2 shows a cross-sectional depiction of a side view of a GRIN lens array at 45 degrees viewing a fingerprint image illuminated at 45 degrees, providing a high contrast strip image on a linear array sensor.

In FIG. 2, a general embodiment of the fingerprint sensor is shown. Surface mount technology (SMT) is used to mount the electronic components of linear array sensor package 8 and linear array light emitting diode (LED) light source 2 onto printed circuit board (PCB) 9. The linear array sensor 4 silicon chip is supported by sensor package 8, and connected by wire bonds 4a. Linear array sensor 4 may have one linear array of light sensing pixels, or two or more parallel linear arrays. Sensor package 8 also supports transparent platen 1. Platen 1 also serves as a cover for package 8, providing a sealed enclosure for linear array sensor 4. GRIN lens array 3 is fitted or otherwise attached to platen 1 such that GRIN lens array 3 is at the appropriate position that it is able to focus on interior surface 1a of platen 1 and also on linear sensor array 4. [Since GRIN lens array 3 projects a narrow strip image onto linear array sensor 4, the orientation of linear array sensor 4 may be varied from that depicted in FIG. 2; for example, the pixel sensing surface of linear array sensor 4 may also tilted so that it is normal to the axis of light 2c coming from GRIN lens array 3.] The top surface of platen 1 of the fingerprint sensor protrudes slightly through a hole in cover surface 12, which may be part of an enclosure for the sensor. A finger with fingerprint 5 is wiped over the top of the sensor platen to obtain a fingerprint image.

In the embodiment shown in FIG. 2, linear array LED light source 2 generates light beam 2a, which ideally is a collimated sheet of monochromatic light which is the width of the fingerprint. Light beam 2a shines upward into the transparent platen 1 where it is reflected by TIR on interior surface 1c and then is directed towards the top interior surface 1a of the transparent platen 1. The skin of fingerprint 5 touches the exterior surface of the platen 1 above position 1a, which causes FTIR where the fingerprint ridges touch the platen, resulting in dark regions for fingerprint ridges and bright regions for fingerprint valleys. The linear strip of high contrast fingerprint image 2b is directed towards GRIN lens array 3, which then focuses light 2c of the fingerprint strip on the width linear array sensor 4.

FIG. 2 also shows several optional refinements which can improve performance. The top of platen 1 has a slightly raised strip 1b which provides increased pressure of the fingerprint on the platen, improving image quality by causing the skin to contact the platen more firmly. Interior surface 1c of platen 1 is roughened to act as a reflective diffuser to light beam 2a to provide more constant illumination across the width of the fingerprint. Surface 1f of platen 1 is blackened to eliminate stray light from reaching linear array 4. On the top surface of platen 1 is sponge or other absorbent or capillary material 11, which optionally is glued into a recess in platen 1 and which can be loaded with water or oil or other lubricating fluid. The function of sponge 11 is to wet the skin of fingerprint 5 before it passes over platen 1 on raised strip 1b, providing a higher contrast image and compensating for dry skin on the fingerprint. A particular advantage of sponge 11 is that it automatically lubricates the finger in a single swiping motion, as the fingerprint image is being taken.

In FIG. 2, and in all embodiments of the invention shown in FIG. 3 through FIG. 11, linear array sensor 4 generates an electronic signal representative of the current strip of the fingerprint image being viewed by the CIS optical system in platen 1. However, unlike a document scanner, where paper 5 is moved over the CIS sensor at a predetermined regular speed by an electric motor, a CIS sensor for fingerprint imaging must accommodate variable and unknown speed of motion of the finger as it is wiped over platen 1. A simple method to measure the speed of motion of the finger is to employ an external sensor. The measurement of the speed of finger motion can used to rectify the image data from linear array sensor 4 to obtain geometrically correct fingerprint images. A second preferred method of measuring finger speed is to compare successive scans of parallel linear arrays in linear array sensor 4. This method of estimating finger speed from linear array sensors is disclosed in commonly owned U.S. patent application 08/892,577 filed Jul. 16, 1997, now U.S. Pat. No. 6,002,815, for an invention called "Linear Sensor Imaging Method and Apparatus."

Figure 3:
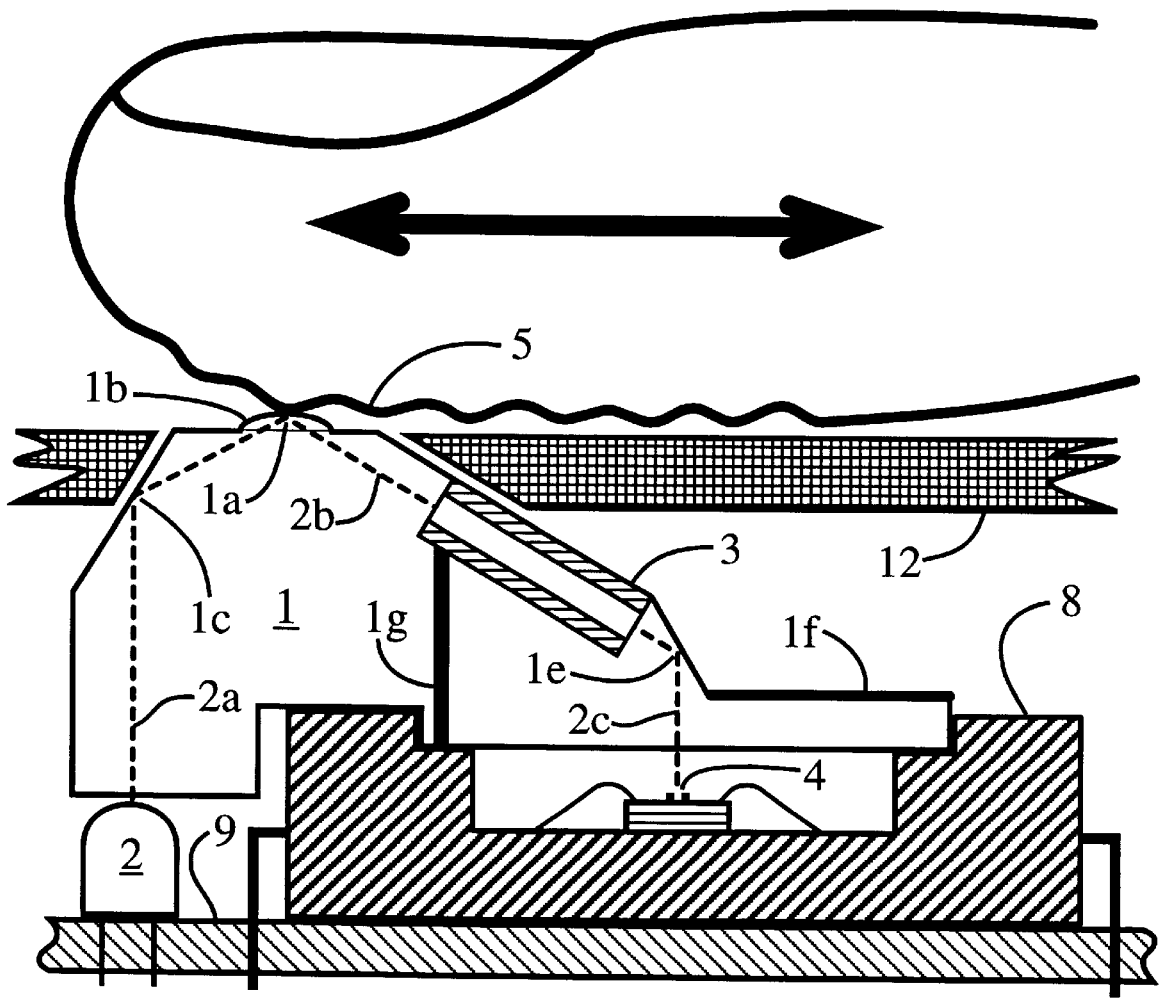
FIG. 3 shows a cross-sectional depiction of a side view of a illuminated fingerprint, with light introduced from the bottom and reflected by total internal reflection, a GRIN lens array mounted at an angle less than 45 degrees to the horizontal, with the projected high contrast image from the GRIN lens array reflected one time by total internal reflection and then directed onto a linear array sensor.

FIG. 3 shows a cross sectional view of another practical embodiment of a fingerprint sensor, employing through-hole technology electronic components of linear array sensor package 8 and linear array LED light source 2 soldered to PCB 9. The linear array sensor 4 silicon chip is supported by sensor package 8, which also supports transparent platen 1. GRIN lens array 3 is fitted or otherwise attached to platen 1 such that the focal distance is appropriate for imaging the fingerprint onto linear array sensor 4. Platen 1 also serves as a cover for package 8, providing a sealed enclosure for linear sensor array 4. The top surface of platen 1 of the fingerprint sensor protrudes slightly through a hole in cover surface 12, which represents part of the sensor enclosure. In this embodiment, the linear array LED light source 2 shines collimated sheet of light 2a upward into the transparent platen 1 where it is bounced by TIR or mirror reflection on interior surface 1c towards interior surface 1a. The skin of fingerprint 5 touches the exterior surface of the platen 1 above position 1a, which causes FTIR reflection of a linear strip of the fingerprint image 2b towards GRIN lens array 3. Light 2c from GRIN lens array 3 is reflected by TIR or a mirrored surface on the interior surface 1e of platen 1, and is then directed downward and focused across the width of linear array sensor 4. If a mirrored surface is employed at surface 1e, the reflective layer may be applied to the external surface of platen 1. The optical design shown in FIG. 3, with a single TIR or mirrored reflection of the fingerprint image on the interior surface 1e of platen 1, causes the image of the fingerprint on linear array sensor 4 to be both foreshortened and directionally reversed in relation to the direction of motion of the fingerprint; the foreshortening and directional reversal are easily characterized and accommodated for by adjustments in the electronic readout of linear array sensor 4.

FIG. 3 also shows several optional refinements which can improve performance. The top of platen 1 has a slightly raised strip 1b, made from silicone rubber or other flexible or rigid transparent material, which provides increased local pressure of the fingerprint on the platen and also increased optical contact between the fingerprint and the flexible top of the platen, improving image quality. Surface 1f of platen 1 is blackened to reduce stray light reaching linear array 4. Lastly, surface 1g inside platen 1 acts as a barrier to eliminate stray light from beam 2a reaching linear array 4.

Figure 4:
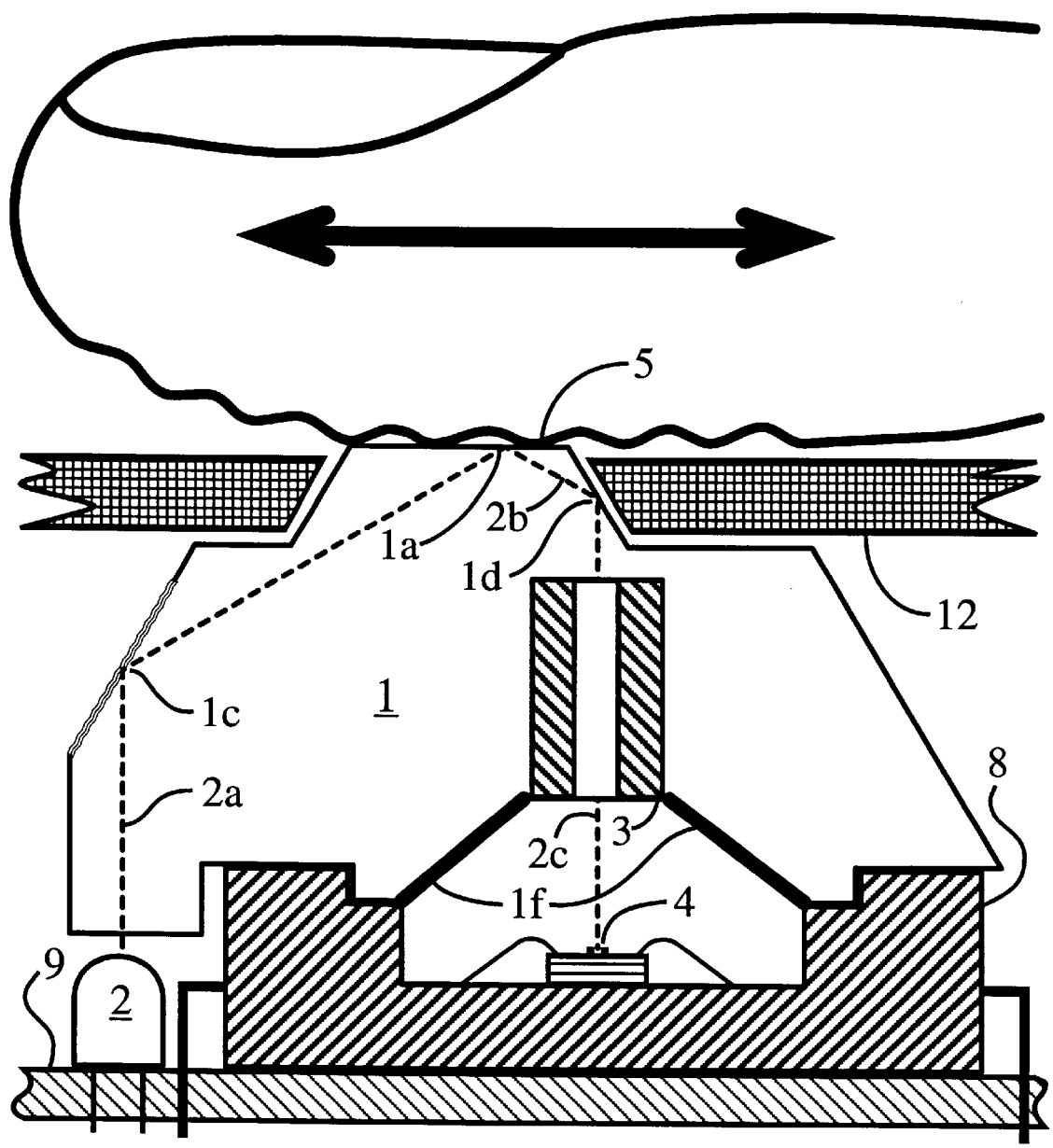
FIG. 4 shows a cross-sectional depiction of a side view of a vertically mounted GRIN lens array viewing a fingerprint, with light introduced from the bottom and reflected by total internal reflection to the fingerprint, the image of the fingerprint reflected to the GRIN lens array by total internal reflection, which then projects a high contrast image of a fingerprint directly onto the linear array sensor.

FIG. 4 shows a cross sectional view of another practical embodiment of a fingerprint sensor, employing through-hole technology electronic components: linear array sensor package 8 and linear array LED light source 2 soldered to PCB 9. The linear array sensor 4 silicon chip is supported by sensor package 8, which also supports transparent platen 1. GRIN lens array 3 is fitted or otherwise attached to platen 1. Platen 1 also serves as a cover for package 8, providing a sealed enclosure for linear sensor array 4 and GRIN lens array 3. The top surface of platen 1 of the fingerprint sensor protrudes slightly through a hole in cover surface 12, which encloses the sensor. In this embodiment, the linear array LED light source 2 shines collimated sheet of light 2a upward into the transparent platen 1 where it is bounced by TIR on interior surface 1c towards interior surface 1a. The skin of fingerprint 5 touches the exterior surface of the platen 1 above position 1a, which causes FTIR reflection of a linear strip of the fingerprint image 2b towards interior surface 1d where it is reflected by TIR or a mirrored surface towards GRIN lens array 3. If a mirrored surface is employed at surface 1d, the reflective layer may be applied to the external surface of platen 1. Light 2c from GRIN lens array 3 is then directed downward and focused across the width of linear array sensor 4. The optical design shown in FIG. 4, with a single TIR or mirror reflection of the fingerprint image on the interior surface 1d of platen 1, causes the image of the fingerprint on linear array sensor 4 to be both foreshortened and directionally reversed, in relation to the direction of motion of the fingerprint; the foreshortening and directional reversal are easily characterized and accommodated for by adjustments in the electronic readout of linear array sensor 4.

FIG. 4 also shows two optional refinements which can improve performance. Surface 1f of platen 1 is blackened to reduce stray light reaching linear array 4. Interior surface 1c of platen 1 is roughened to act as a reflective diffuser to light beam 2a to provide more constant illumination across the width of the fingerprint.

Figure 5:
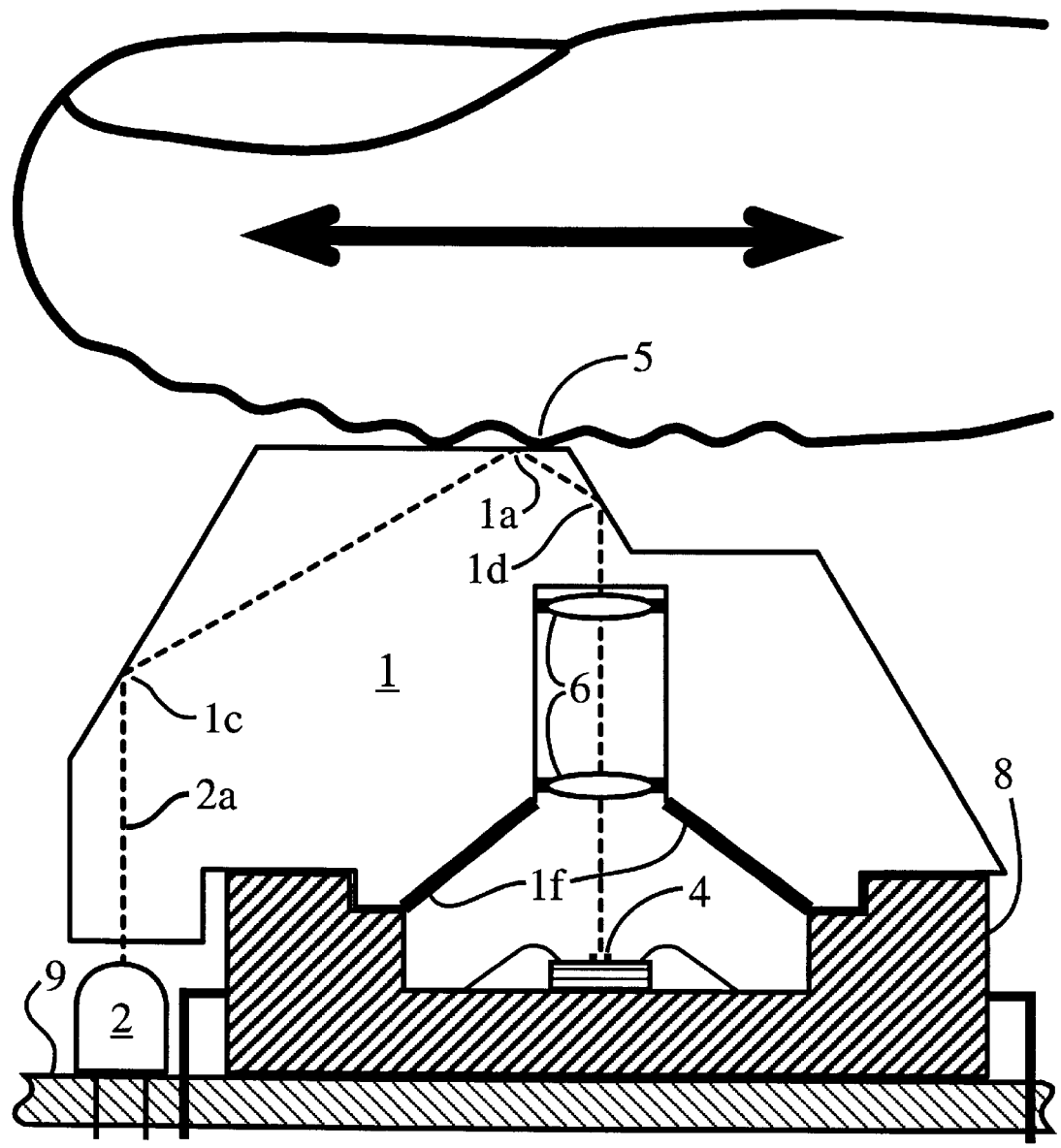
FIG. 5 shows a view of an optical system identical to that in FIG. 4, with the exception that an array of small relay optics lens pairs has been substituted equivalently for the GRIN lens.

FIG. 5 shows a cross sectional view of another practical embodiment of a fingerprint sensor, employing through-hole technology electronic components of linear array sensor package 8 and linear array LED light source 2 soldered to PCB 9. The linear array sensor 4 silicon chip is supported by sensor package 8, which also supports transparent platen 1. Relay lens array 6 is fitted or otherwise attached inside platen 1 such that it projects an image of fingerprint 4 on linear array sensor 4. Platen 1 also serves as a cover for package 8, providing a sealed enclosure for linear sensor array 4 and relay lens array 6. In this embodiment, the fingerprint image is acquired in a manner identical to FIG. 4, with the exception that relay lens array 6 is used in place of a GRIN lens array. As an optional refinement, surface 1f of platen 1 is blackened to reduce stray light reaching linear array 4.

Figure 6:
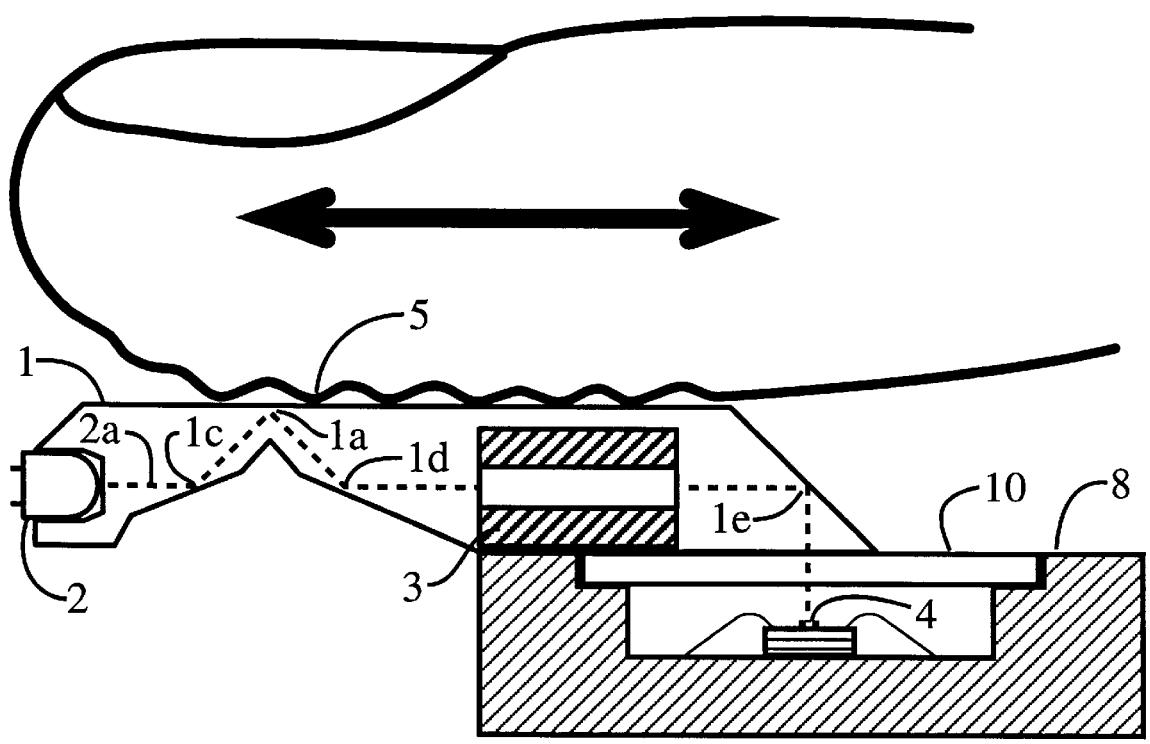
FIG. 6 shows a cross-sectional depiction of a side view of a horizontally deployed GRIN lens array viewing an illuminated fingerprint, with light introduced horizontally from the side and reflected by total internal reflection to the fingerprint, and the image of the fingerprint reflected by total internal reflection to the GRIN lens array and thereafter reflected again by total internal reflection down onto the linear array sensor.

FIG. 6 shows a cross sectional view of a more compact embodiment of a fingerprint sensor. The linear array sensor 4 silicon chip is sealed inside sensor package 8 by transparent glass or plastic cover 10. Platen 1 is held in place over sensor package 8 and cover 10 by glue or other attachment or supporting means. GRIN lens array 3 and linear array LED light source 2 are fitted or otherwise attached to platen 1. Linear array LED light source 2 shines collimated light sheet 2a sideways into the transparent platen 1 where it is bounced by TIR or mirror reflection on interior surface 1c towards the top interior surface 1a of the transparent platen 1. The skin of fingerprint 5 touches the exterior surface of the platen 1 above position 1a, which causes a linear strip of the fingerprint image to be reflected by FTIR from 1a towards interior surface 1d, where it is again reflected by TIR or a mirror surface towards GRIN lens array 3. The light from GRIN lens array 3 is then reflected by TIR or mirror reflection by interior surface 1e, which then directs the light downward through cover 10 where the image is focused across the width of linear array sensor 4. If a mirrored surface is employed at surface 1e and/or 1d, the reflective layer may be applied to the external surface of platen 1. The optical design shown in FIG. 6, with two TIR or mirror reflections of the fingerprint image on interior surfaces 1d and 1e of platen 1, causes the image of the fingerprint on linear array sensor 4 to be foreshortened in relation to the direction of finger motion but not directionally reversed; the foreshortening is easily characterized and accommodated by adjustments in the electronic readout of linear array sensor 4.

Figure 7:
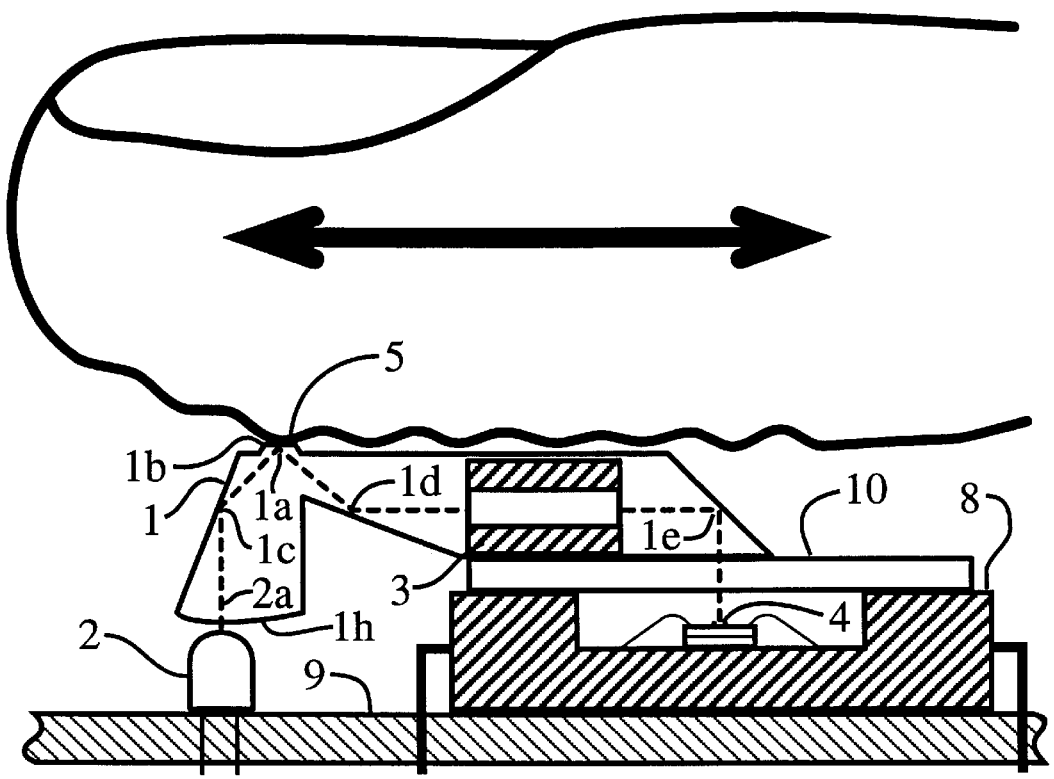
FIG. 7 shows a cross-sectional depiction of a side view of a horizontally deployed GRIN lens array viewing an illuminated fingerprint, with light introduced from the bottom and reflected by total internal reflection to the fingerprint, and the high contrast image of the fingerprint reflected by total internal reflection to the GRIN lens array and thereafter reflected again by total internal reflection down onto the linear array sensor.

FIG. 7 shows a cross sectional view of another compact embodiment of a fingerprint sensor, employing through-hole technology electronic components of linear array sensor package 8 and linear array LED light source 2 soldered to PCB 9. The linear array sensor 4 silicon chip is sealed inside sensor package 8 by transparent plastic or glass cover 10. Platen 1 is supported over cover 10 by glue or other attachment or support means. GRIN lens array 3 is fitted or otherwise attached to platen 1. Linear array LED light source 2 shines upward into the transparent platen 1, through curved surface 1h, which serves as a lens to collimate light inside platen 1, increasing the amount of light available for imaging the fingerprint. Light from light source 2 is bounced by TIR or mirror reflection on interior surface 1c towards the top interior surface 1a of the transparent platen 1. The skin of fingerprint 5 touches the exterior surface of the platen 1 above position 1a, which causes a linear strip of the fingerprint image to be reflected by FTIR from 1a towards interior surface 1d, where it is again reflected by TIR or mirror reflection towards GRIN lens array 3. The narrow strip image from GRIN lens array 3 is then reflected by TIR or mirror reflection on interior surface 1e, which directs the image downward through cover 10 where it is focused across the width of linear sensor array 4. If a mirrored surface is employed at surface 1e and/or 1d, the reflective layer may be applied to the external surface of platen 1. In this embodiment, the upper interior surface 1a of the platen 1 is contained in a slightly raised strip 1b which provides increased pressure of the fingerprint onto the platen imaging surface above 1a, improving image quality. As in FIG. 6, the image on linear array 4 is foreshortened but not reversed in direction.

Figure 8:
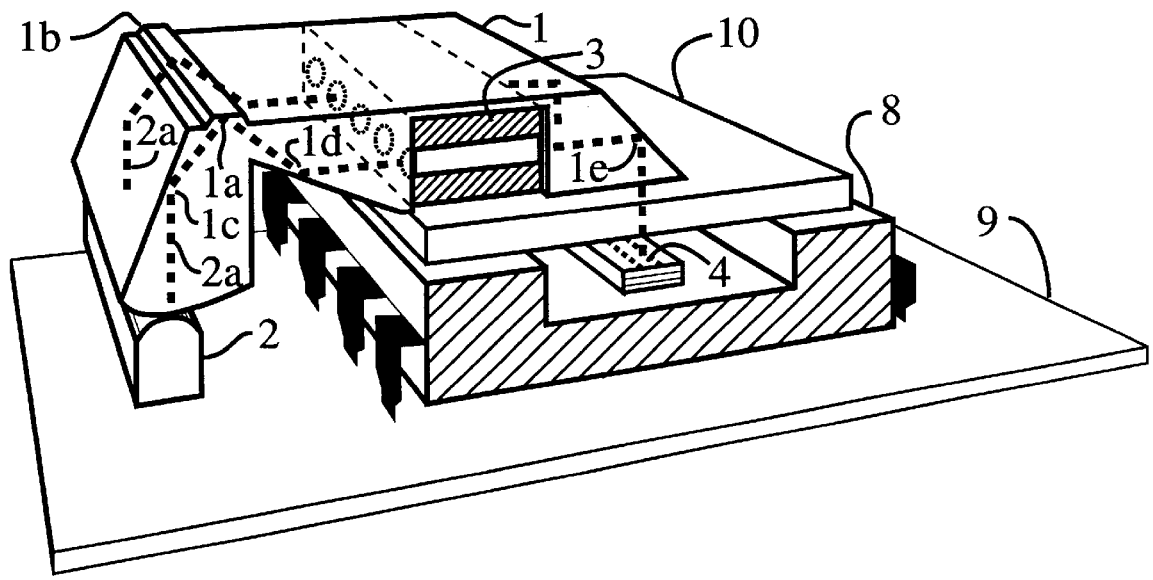
FIG. 8 shows a cross-sectional perspective view of an optical system identical to that shown in FIG. 7.

FIG. 8 shows a perspective view of the embodiment shown in FIG. 7, with the electronic components of linear array sensor package 8 and linear array LED light source 2 soldered to PCB 9; in this perspective view, the ends of the sensor package are cut off for display purposes. In this view, the width of the fingerprint sensor, as measured along the width of transparent platen 1 and raised strip 1b, is about 19 mm, or the approximate width of the human finger, although variations in this dimension will also function satisfactorily. GRIN lens array 3 is at least the width of linear sensor array 4 and is fitted or otherwise attached to platen 1 to properly focus the fingerprint image on linear sensor array 4. Light source 2 can be seen as a linear bar of multiple linear array LEDs, or any other elongated light source, providing an upwardly directed sheet of approximately collimated light 2a, which is also the width of the fingerprint sensor. The sheet of light of light beam 2a is directed into platen 1 and reflected internally by TIR or mirror reflection at internal surface 1c in platen 1 onto interior surface 1a, illuminating the width of raised strip 1b of platen 1. When the skin of a fingerprint is pressed against the raised surface of strip 1b, the fingerprint ridges cause FTIR and absorb light at position 1a, while the valleys of the fingerprint do not touch the platen and thus allow light to be reflected by TIR from interior surface 1a. The narrow strip fingerprint image from the width surface 1a is reflected by TIR or mirror reflection along the width of interior surface 1d and is directed towards GRIN lens array 3. GRIN lens array 3 acts in the manner of a relay lens and refracts the fingerprint strip image and sends the image to be reflected again by TIR or mirror reflection along the width interior surface 1e, which then directs the image downward through glass or plastic cover 10 where the image of the narrow fingerprint strip is focused across the width of linear sensor array 4. If a mirrored surface is employed at surface 1e and/or 1d, the reflective layer may be applied to the external surface of platen 1.

Figure 9:
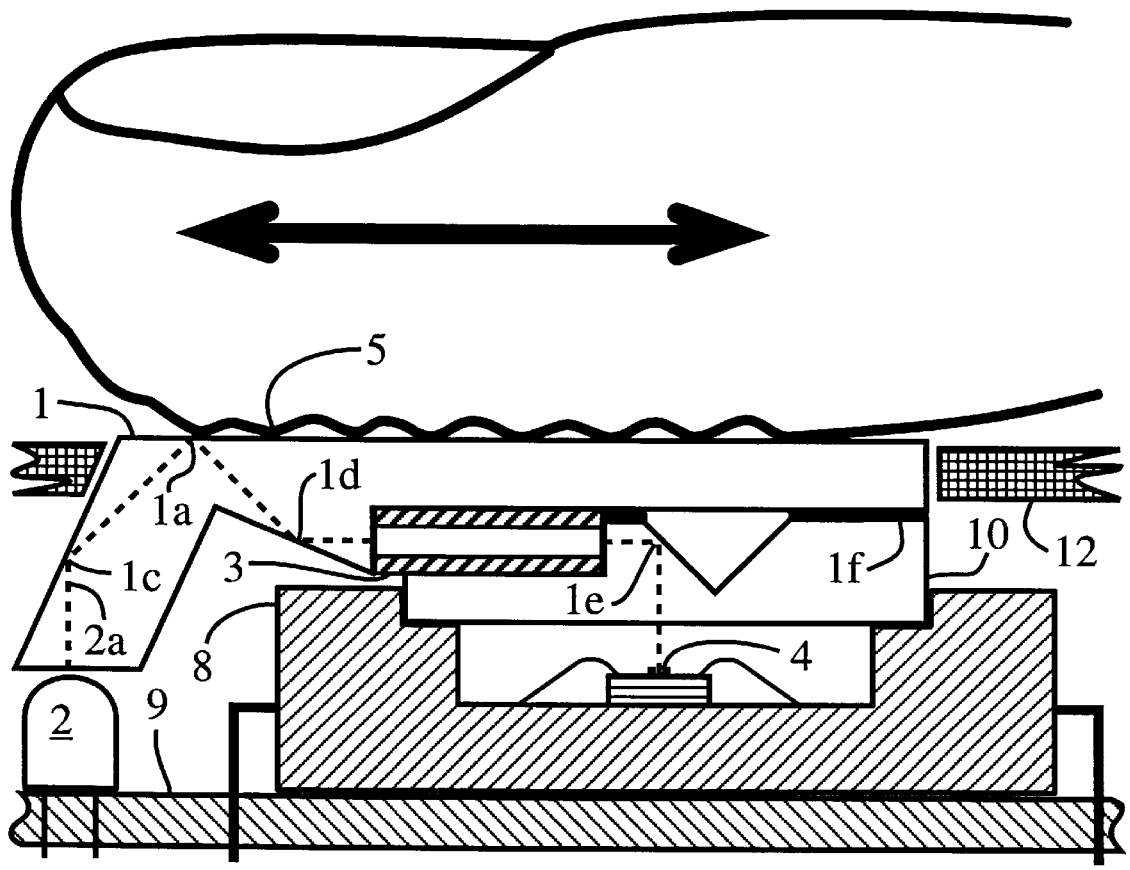
FIG. 9 shows a cross-sectional view of an optical system similar to that shown in FIG. 7, with the exception that the GRIN lens array is supported by two transparent optical elements.

FIG. 9 shows a cross sectional view of a practical embodiment similar to that shown in FIG. 7, employing through-hole technology electronic components of linear array sensor package 8 and linear array LED light source 2 soldered to PCB 9. In this embodiment, the function of the transparent platen is separated into two parts. Platen 1 is attached to cover 10 by glue or other attachment means. The linear array sensor 4 silicon chip is sealed inside sensor package 8 by transparent plastic or glass cover 10, which also serves as part of the optical path to reflect the fingerprint image from interior surface 1e. GRIN lens array 3 is fitted or otherwise attached between platen 1 and cover 10; opaque layer 1f serves to limit unwanted light from reaching linear array sensor 4. The top surface of platen 1 of the fingerprint sensor protrudes slightly through a hole in cover surface 12, which is part of an enclosure for the sensor. Linear array LED light source 2 shines upward into the transparent platen 1. The collimated sheet of light 2a is bounced by TIR or mirror reflection on interior surface 1c towards top interior surface 1a of the transparent platen 1. The skin of fingerprint 5 touches the exterior surface of the platen 1 above position 1a, which causes a linear strip of the fingerprint image to be reflected by FTIR from 1a towards interior surface 1d, where it is again reflected by TIR or mirror reflection towards GRIN lens array 3. The narrow strip image from GRIN lens array 3 is then reflected by TIR or mirror reflection on interior surface 1e, which directs the image downward through cover 10 where it is focused across the width of linear sensor array 4. If a mirrored surface is employed at surface 1e and/or 1d, the reflective layer may be applied to the external surface of platen 1. As in FIG. 7, the image on linear array 4 is foreshortened but not reversed in direction.

Figure 10:
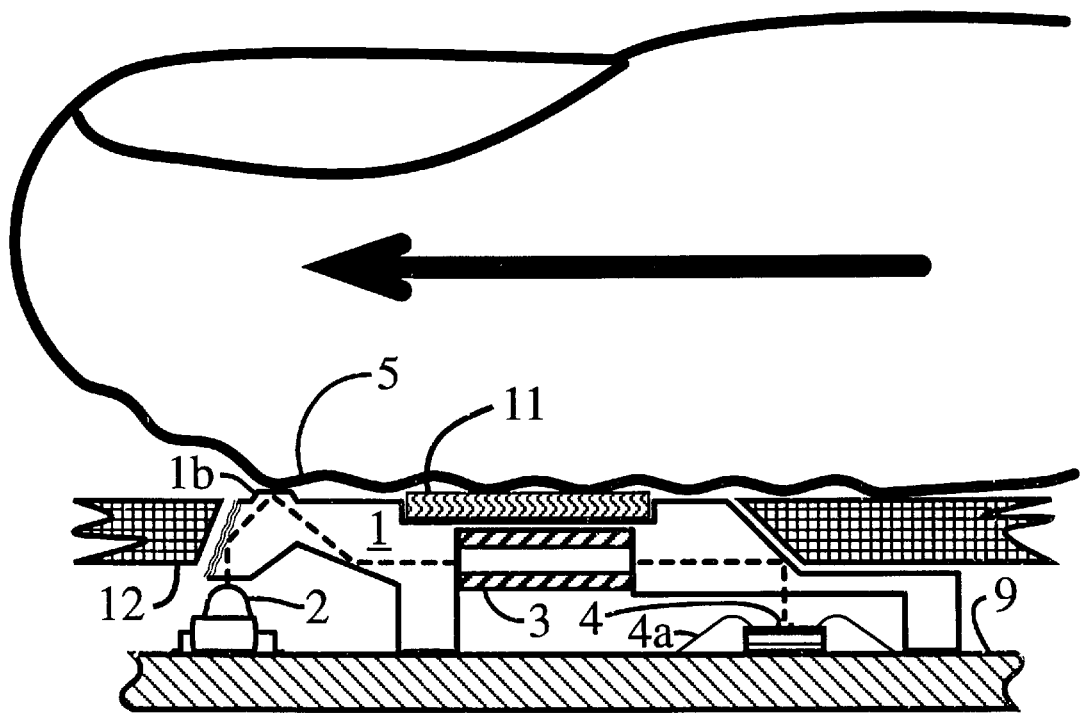
FIG. 10 shows a cross-sectional view of an optical system similar to that shown in FIG. 7, with the exception that the linear array sensor is mounted directly on the PC board, as a chip-on-board mounting, eliminating the need for a package for the linear array sensor.

FIG. 10 shows a cross sectional view of a practical miniaturized embodiment, employing chip-on-board (COB) mounting with wire-bonding 4a for the linear array sensor 4 and SMT for the linear array LED light source 2, both attached to PCB 9. The elimination of a package for linear array sensor 4 allows for further miniaturization of the fingerprint sensor. In this embodiment, platen 1 is designed to be glued or otherwise attached to PCB 9 and to completely cover linear array sensor 4, protecting it from the environment. GRIN lens array 3 is fitted or otherwise attached to platen 1. The fingerprint is optically sensed in a manner identical to that shown in FIG. 7. In this embodiment, the upper interior surface 1a of the platen 1 is contained in a slightly raised strip 1b which provides increased pressure of the fingerprint onto the platen imaging surface above 1a, improving image quality. As in FIG. 2, a sponge or other absorbent or capillary material 11 serves to supply a fluid to the skin of the fingerprint, providing increased optical contact with platen 1. The top surface of platen 1 of the fingerprint sensor protrudes slightly through a hole in cover surface 12, which encloses the sensor.

Figure 11:
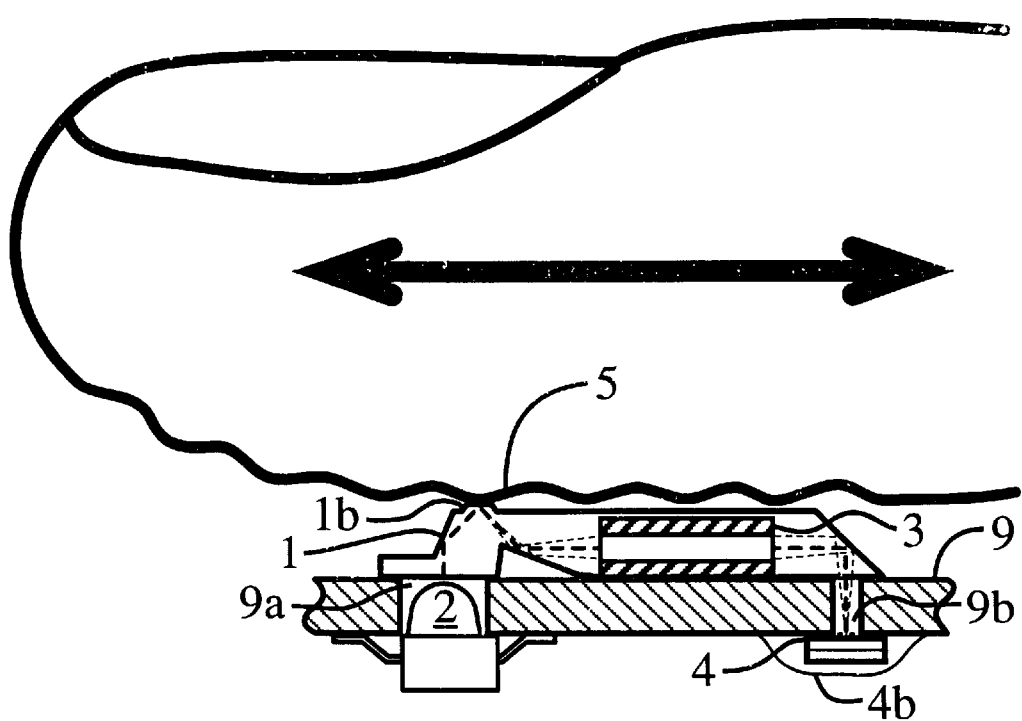
FIG. 11 shows a cross-sectional view of an optical system similar to that shown in FIG. 7, with exception that the optical elements are attached directly to the PC board, and the linear array sensor is mounted as a flip-chip on the opposite side of the PC board, over a slot in the board, which allows light to reach the linear array sensor surface.

FIG. 11 show a cross sectional view of a practical sub-miniaturized fingerprint sensor. Components are mounted on both sides of PCB 9. On the bottom surface of PCB 9 is mounted linear array LED light source 2, which shines a sheet of light upward through a slotted hole 9a or multiple single holes. Also on the bottom surface of PCB 9 is linear array sensor 4, which is mounted using "flip-chip" technology, which either bonds the chip to the printed circuit board with pressure-welds which also provide the required electrical contacts, or is mounted using special conductive glue to bond the electrical contacts and hold the chip to the printed circuit board; epoxy coating 4b, or other suitable material, may be used to protect linear array sensor 4. Since linear array sensor 4 must be bonded to the PCB with pixels directed towards the opposite side of the board, slotted hole 9b is provided to allow light to shine on the pixels. On the top surface of PCB 9 is glued or otherwise mounted platen 1. GRIN lens array 3 is fitted or otherwise attached to platen 1. In this configuration, the optical path is otherwise similar to that shown in FIG. 7.

The above descriptions of apparatus are examples of means to implement the method of creating an electronic image of a finger.

While the principles of the invention have now been made clear in the illustrated embodiments, there will be immediately obvious to those skilled in the art, many modifications of structure, arrangements, proportions, the elements, materials and components used in the practice of the invention, and otherwise, which are particularly adapted for specific environments and operational requirements without departing from those principles. The claims are therefore intended to cover and embrace such modifications within the limits only of the true spirit and scope of the invention. In particular, it will be appreciated that while a finger has been described for the creation of an electronic image of a fingerprint, other objects having ridges or varied surfaces (e.g. toes, noses and other human parts as well as inanimate surfaces) are encompassed by the present invention.

What is claimed is:

1. Imaging apparatus, comprising:
    a. platen composed of a clear, optically transparent material with a surface for the skin of the finger
    b. light source, shining so as to reflect light off the interior surface of the platen adjacent to the skin of the finger, such light reflected by total internal reflection or frustrated total internal reflection
    c. GRIN lens array, situated in contact with or at least partially within said platen, to focus the light reflected from the top interior surface of the platen onto
    d. linear sensor array.

2. Imaging apparatus of claim 1, further having multiple parallel linear sensor arrays.

3. Imaging apparatus of claim 1, further having the light from the light source redirected by a reflection on an interior surface of the platen using a mirror or total internal reflection.

4. Imaging apparatus of claim 3, further having the light from the light source redirected by a reflection on an interior surface of the platen which is roughened.

5. Imaging apparatus of claim 3, further having the light from the light source collimated by lens molded into the platen where the light enters.

6. Imaging apparatus of claim 1, further having a ridge on the top of the platen, either formed from the platen material or a different optically transparent material.

7. Imaging apparatus of claim 1, further having the light from the platen surface reflected on an interior surface using a mirror or total internal reflection before entering the focus means.

8. Imaging apparatus of claim 1, further having the light from the focusing means reflected on an interior surface using a mirror or total internal reflection before arriving at the linear sensor array.

9. Imaging apparatus of claim 1, further having a reservoir for liquid embedded in the platen surface.

10. Imaging apparatus of claim 1, further having blackened faces of the platen.

11. Imaging apparatus of claim 1, further employing a method of sensing and measuring finger motion speed and correcting for geometric errors in the electronic output image.

12. Imaging apparatus of claim 11 further comprising the features of any one of claims 2 to 6 or 7 to 10.

13. A method of creating an image of an object with a varied surface, comprising the steps of:
  (a) moving the object over a transparent ridge on a transparent platen,
  (b) shining a light from underneath;
  (c) collecting the resulting total internal reflection and frustrated total internal reflection and directing to a linear array sensor to create an electronic image of the object thereon.

14. The method of claim 13 further comprising the step of:
  (d) measuring object motion speed and correcting for geometric errors in said electronic image.

15. Imaging apparatus, comprising:
  a. a platen composed of a clear, optically transparent material with a surface for the skin of the finger
  b. a light source, shining so as to reflect light off the interior surface of the platen adjacent to the skin of the finger, such light reflected by total internal reflection or frustrated total internal reflection
  c. a relay lens array, situated to focus the light reflected from the top interior surface of the platen onto
  d. a linear sensor array.

16. Imaging apparatus of claim 15, further having multiple parallel linear sensor arrays.

17. Imaging apparatus of claim 15, further having a ridge on the top of the platen, either formed from the platen material or a different optically transparent material.

18. Imaging apparatus of claim 15, further having the light from the platen surface reflected on an interior surface using a mirror or total internal reflection before entering the focus means.

19. Imaging apparatus of claim 15, further employing a method of sensing and measuring finger motion speed and correcting for geometric errors in the electronic output image.

20. Imaging apparatus, comprising:
  a. a platen composed of a clear, optically transparent material with a surface for the skin of the finger
  b. a light source, shining so as to reflect light off the interior surface of the platen adjacent to the skin of the finger, such light reflected by total internal reflection or frustrated total internal reflection
  c. a GRIN lens array, situated to focus the light reflected from the top interior surface of the platen onto
  d. multiple parallel linear sensor arrays.

21. Imaging apparatus, comprising:
  a. a platen composed of a clear, optically transparent material with a surface for the skin of the finger
  b. a light source, shining so as to reflect light off a roughened interior surface of the platen adjacent to the skin of the finger, such light reflected by total internal reflection or frustrated total internal reflection, such light redirected by a reflection on an interior surface of the platen using a mirror or total internal reflection,
  c. GRIN lens array, situated to focus the light reflected from the top interior surface of the platen onto
  d. linear sensor array.

22. Imaging apparatus, comprising:
  a. a platen composed of a clear, optically transparent material with a surface for the skin of the finger
  b. a light source, shining so as to reflect light collimated by a lens molded into the platen, off the interior surface of the platen adjacent to the skin of the finger, such light reflected by total internal reflection or frustrated total internal reflection, such light redirected by a reflection on an interior surface of the platen using a mirror or total internal reflection,
  c. a GRIN lens array, situated to focus the light reflected from the top interior surface of the platen onto
  d. a linear sensor array.

23. Imaging apparatus, comprising:
  a. a platen composed of a clear, optically transparent material with a surface for the skin of the finger, the platen having a ridge on the top of the platen either formed from the platen material or a different optically transparent material;
  b. a light source, shining so as to reflect light off the interior surface of the platen adjacent to the skin of the finger, such light reflected by total internal reflection or frustrated total internal reflection
  c. a GRIN lens array, situated to focus the light reflected from the top interior surface of the platen onto
  d. a linear sensor array.

24. Imaging apparatus, comprising:
  a. a platen composed of a clear, optically transparent material with a surface for the skin of the finger
  b. a light source, shining so as to reflect light off the interior surface of the platen adjacent to the skin of the finger, such light reflected by total internal reflection or frustrated total internal reflection
  c. a GRIN lens array, situated to focus the light reflected from the top interior surface of the platen, such focused light reflected on an interior surface using a mirror or total internal reflection onto,
  d. a linear sensor array.

25. Imaging apparatus, comprising:
  a. a platen composed of a clear, optically transparent material with a surface for the skin of the finger
  b. a reservoir for liquid embedded in the platen surface;
  c. a light source, shining so as to reflect light off the interior surface of the platen adjacent to the skin of the finger, such light reflected by total internal reflection or frustrated total internal reflection
  d. a GRIN lens array, situated to focus the light reflected from the top interior surface of the platen onto
  e. a linear sensor array.

* * * * *